(12) United States Patent
Rosenblum et al.

(10) Patent No.: US 6,669,938 B1
(45) Date of Patent: Dec. 30, 2003

(54) IMMUNOCONJUCATES FOR CANCER DIAGNOSIS AND THERAPY

(75) Inventors: Michael G. Rosenblum, Sugar Land, TX (US); Renato Dulbecco, La Jolla, CA (US); W. Ross Allen, Encinitas, CA (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 08/201,134

(22) Filed: Sep. 24, 1993

Related U.S. Application Data

(63) Continuation of application No. 07/839,729, filed on Feb. 19, 1992, now abandoned, which is a continuation of application No. 07/216,595, filed on Jul. 7, 1988, now abandoned.

(51) Int. Cl.$^7$ .......................... C12P 21/08; A61K 39/44; A61K 39/395
(52) U.S. Cl. ................... 424/183.1; 424/156.1; 424/178.1; 424/85.1; 424/85.2; 424/85.4; 530/391.7; 530/388.15
(58) Field of Search ................ 424/85.1, 85.2, 424/85.4, 183.1, 156.1, 178.1; 530/388.15, 391.7

(56) References Cited

U.S. PATENT DOCUMENTS

| | | | | |
|---|---|---|---|---|
| 4,263,279 A | * | 4/1981 | Sela et al. ................ | 424/85 |
| 4,440,747 A | | 4/1984 | Neville Jr. et al. ........ | 424/85.91 |
| 4,520,226 A | | 5/1985 | Neville, Jr. et al. ....... | 424/85.91 |
| 4,731,238 A | | 3/1988 | Neville et al. ............ | 424/85.91 |
| 4,753,894 A | * | 6/1988 | Frankel et al. ............ | 436/548 |
| 4,771,128 A | * | 9/1988 | Ferris et al. .............. | 530/417 |
| 4,801,578 A | * | 1/1989 | Monsigny et al. .......... | 514/8 |
| 4,831,122 A | * | 5/1989 | Buchsbaum et al. ........ | 530/389 |

FOREIGN PATENT DOCUMENTS

| | | | | |
|---|---|---|---|---|
| EP | 153114 | | 8/1985 | ............ 435/68 |
| EP | 154114 | * | 8/1985 | ........... C12P/21/00 |
| EP | 184369 | * | 6/1986 | ........... C12P/21/00 |
| EP | 226418 | | 6/1987 | ............ 530/389 |
| EP | 216714 | | 2/1988 | ............ 424/85.91 |
| EP | 256471 | | 2/1988 | ............ 424/85.91 |
| JP | 6220909 | | 9/1987 | ............ 424/85.9 |
| WO | 8501299 | | 9/1986 | ............ 424/88 |
| WO | WO 86/05098 | * | 9/1986 | |

OTHER PUBLICATIONS

Hann et al., Curr. Opin. Cell Biol. 13:778–784, 2001.*
Green et al., Cancer Treatment Reviews 26:269–286, 2000.*
White et al., Cancer Research 45:1337–1343, Mar. 1985.*
Freshney, Culture of Animal Cells, A Manual of Basic Technique, Alan R. Liss, Inc., 1983.*
Dermer, Bio/Technology 12:320, 1994.*
Pastan et al (1991) Science 254:1173–1177.*
Vitetta et al (1991) Cancer Res. 51:4052–58.*
Hertler et al. (1988) J. Biol. Response Modifiers 1:97–113.*
Gould et al (1989) J. Natl. Cancer Inst. 81:775–781.*
Akan et al (1984) J. Interferon Res 4(3):355–363.*
Blair et al (1983) J. Immunol. Methods 59:129–143.*
Byers et al (1990) FASEB J 4(7):A1855 Abstract.*
Flannery et al (1984) Eur. J. Can. Oin. Oncol 20(6):791–798.*
Miescher—Ganyer et al (1985) FEBS Lett 179(1):29–33.*
Pelham et al (1983) Cancer Immunol Immunother 15:210–216.*
Splitler et al (1987) Cancer Res 47:1717–1723.*
Wawrzynczak et al (1987) In Immunoconjugate(Vogeled) NY, OxfordP, pp 28–55.*
Till et al (1988) Cancer Res. 48:1119–1123.*
Frankel (1985) J. Biol. Response Modifiers 4: 437–446.*
Gallego J et al "Preparation of Four Daunonycen–Monoclonal Antibody 791T/36 Conjugates with Antitumor Activity" (1984) Int. J. Cancer :33:737–744.*
Arnon et al "Monclonal Antibodies for Immunoconjugates of Drugs in Cancer Therapy" Monoclonal Antibodies and Cancer Therapy 1985 Alan R. Liss, Inc pp. 243–256.*
White CA et al "Two Monoclonal Antibodies Selective for Human Mammary Carcinoma" Cancer Res 45:1337–1343 (1985).*
Mihich, E :"Future Perspectives For Biological Response Modifiers: A Viewpoint" Seminars in Oncology 13(2):234–254 1986.*
Waldmann, TA "Multichain Interleukin–2 Receptor:A Target for Immunotherapy in Lymphoma" J. Can Nat. Can. Inst. 81(12):914–923.*
for Immunotherapy in Lymphoma J. Can Nat. Can. Inst. 81(12):914–923.*
Aboud–Pirak E et al "Cytotoxic Activity of Daunorubicin on Vindes Coujugated to a Monoclonal Antibody on Cultured NCF–7 Breast Carcinoma Cells" Biochem Pharmocology 38(4):641–648 (1989).*
M. J. Bjorn et al., (1985) Cancer Research 45:1214–1221.
Barbieri et a., Cancer Surveys 1(3):489 (1982).
Blakey et al., Cancer Drug Delivery 3(3):189 (1986).
Colombatti et al., Immunology 55:331 (1985).
Colombatti et al., The Journal of Immunology 131(6):3091 (1983).
Colombatti et al., The Journal of Immunology 138(9):3339 (1987).
Descotes et al., Int. J. Immunopharmac. 7(4):455 (1985).
Falasca et al., Biochem. J. 207:505 (1982).

(List continued on next page.)

Primary Examiner—Rebecca E. Prouty
Assistant Examiner—Delia Ramirez
(74) Attorney, Agent, or Firm—Benjamin Aaron Adler

(57) ABSTRACT

Immunoconjugates of an antibody to a 22 KD breast tumor associated antigen were prepared. Cytotoxic immunoconjugates such as gelonin-15A8 antibody conjugate are useful for treating proliferative cell diseases such as breast carcinoma and cervical carcinoma as well as other tumors which bear the 15A8 antigen. Detectably labeled compositions for diagnosis of such diseases are also disclosed.

4 Claims, 7 Drawing Sheets

OTHER PUBLICATIONS

Frankel, *Journal of Biologial Response Modifiers* 4:437 (1985).
Glennie et al., *J. Exp. Med.* 166:43 (1987).
Goldmacher et al., *The Journal of Immunology* 135(6):3648 (1985).
Goldmacher et al., *The Journal of Cell Biology* 102:1312 (1986).
Goldmacher et al., *The Journal of Biological Chemistry* 262(7):3205(1987).
Gregg et al., *The Journal of Immunology* 138(12):4502 (1987).
Hara, et al., *Proc. Nat'l Acad. Sci. USA* 84:3390 (1987).
Lambert et al., *THe Journal of Biological Chemistry* 260(22):12035 (1985).
Lappi et al., *Biochemical and Biophysical Research Communications* 129(3):934 (1985).
Letvin et al., *J. Clinical Investigation* 77:977 (1986).
Letvin et al. *J. Clinical Investigation* 78:666 (1986).
Levin et al., *Cancer Immunol. Immunother,* 24:202 (1987).
McIntosh, et al., *Biochimica et Biophysica Acta* 690:224 (1982).
Morgan, Jr. et al., *JNCI* 78(6):1101 (1987).
Pastan et al., *Cell* 47:641 (1986).
Raso et al., *Cancer Research* 41:2073 (1981).
Roche et al., *Journal of Cellular Biochemistry* 22:131 (1983).
Sargiacomo et al., FEBS Letters 151(1):150 (1983).
Schwartz et al., *Endocrinology* 121(4):1454 (1987).
Schwartz et al., Endocrinology 122(4):1695 (1988).
Scott, et al., *Cancer Immunol. Immunother.* 25:31 (1987).
Scott, et al. *JNCI* 79(5):1163 (1987).
Scott, et al. *Int. J. Immunopharmac* 9(2):211 (1987).
Sikora et al., *Cancer Surveys* 1(3):521 (1982).
Sivam et al., *Cancer Research* 47:3169 (1987).
Srinivasan et al., FEBS Letters 192(1):113 (1985).
Tedder, et al., *The Journal of Immunology* 137(4):1387 (1986).
Thorpe et al., *Eur. J. Biochem.* 116:447 (1981).
Thorpe et al., *Immunological Rev.* 62:119 (1982).
Thorpe et al., *Eur. J. Biochem.* 147:197 (1985).
Vitetta et al., *Science* 219:644 (1983).
Wahl et al., *Cancer Immunol. Immunother.* 24:221 (1987).
J. Weils, et al., *Cancer Research* 44:129 (1984).
Zuckerman et al. *AACR Proceedings* 29:427 (1988).

\* cited by examiner

IMMUNOCONJUCATES FOR CANCER DIAGNOSIS AND THERAPY

CROSS-REFERENCE TO RELATED APPLICATION

This application is a continuation of U.S. Ser. No. 07/839,729, filed Feb. 19, 1992, now abandoned, which is a continuation of U.S. Ser. No. 07/216,595, filed Jul. 7, 1988, now abandoned.

BACKGROUND

1. Field of the Invention

The present invention relates generally to the field of immunoconjugates and, more particularly, to the use of immunoconjugates in the diagnosis and treatment of cancer. The invention also relates to the treatment of breast and cervical carcinoma with cytotoxic conjugates of monoclonal antibodies (MoAbs) and gelonin, a ribosomal inhibiting protein.

2. Background of the Invention

Breast cancer and cervical cancer are two of the leading causes of death from malignancy in women in the Western world. Surgical removal of localized malignancies has proven effective only when the disease has not spread beyond the primary lesion. Once the disease has spread, the surgical procedures must be supplemented with other more general procedures to eradicate the diseased or malignant cells. Most of the commonly utilized supplementary procedures such as irradiation or chemotherapy are not localized to the tumor cells and, although they have a proportionally greater destructive effect on malignant cells, often affect normal cells to some extent.

Many tumors express antigens or antigenic determinants which are either expressed very weakly or not expressed at all by normal cells. Some tumor cells express antigens which are expressed by embryonic cell types but are not expressed by normal cells of a mature animal. These abnormally expressed antigens are known as tumor-associated antigens. The antigens expressed by tumors are specific in that while a particular antigen may be expressed by more than one tumor, it is usually expressed by all or most cells of the particular tumors which express it. A tumor cell may express one or more than one tumor-associated antigen. These tumor-associated antigens may be expressed on the surface of the cell (cell surface antigen), may be secreted by the tumor cell (secreted antigens) or may remain inside the cell (intercellular antigen).

The presence of these tumor-associated antigens has been utilized to detect, diagnose and localize the tumor. In some cases the presence of the tumor-associated antigens on the tumor cells has allowed the targeting of specific drugs and treatment means specifically to the tumor cells.

Antibodies are proteins normally produced by the immune system of an animal in response to foreign antigens or antigenic determinants. Antibodies bind to the specific antigen to which they are directed. Monoclonal antibodies directed to specific antigens or antigenic determinants may be prepared in large quantities.

One method of targeting chemotherapeutic agents to tumor cells and to diminishing their effects on normal cells has been made possible with the development of MoAbs directed against antigens on the tumor cells which do not occur on normal cells.

Antibodies may be labelled in order to allow their use for localization and treatment of malignant diseases. Antibodies, coupled to drugs, may be used as a delivery system by which the drug is targeted to a specific tumor cell type against which the antibody is directed. Antibodies may also be coupled to toxins and thus act as a delivery system to target the toxins directly to specific tumor cells.

Gelonin is a glycoprotein (M.W. 29–30,000) purified from the seeds of *Gelonium multiforum*. Gelonin belongs to a class of potent ribosomal inactivating plant toxins. Other members of this class of ribosomal inactivating plant toxins are the chains of Abrin, Ricin and Modeccin. Gelonin, like abrin and ricin, inhibits protein synthesis by damaging the 60S sub-unit of mammalian ribosomes. The inactivation of ribosomes is irreversible, does not appear to involve co-factors and occurs with an efficiency which suggests that Gelonin acts enzymatically.

Numerous prior workers have suggested or reported linking cytotoxic agents to antibodies to make "immunotoxins." Of particular interest have been immunotoxins of monoclonal antibodies conjugated to the enzymatically active portions (A chains) of toxins of bacterial or plant origin such as Ricin or Abrin. Nevelle and York, *Immunol. Rev.* (1982) 62: 75–91; Ross et al., *European J. Biochem.* (1980) 104; Vitteta et al., *Immunol. Rev.* (1982) 62: 158–183; Ross et al., *Cancer Res.* (1982) 42: 457–464; Trowbridge and Domingo *Nature (Cond.)* (1981) 294: 171–173.

Gelonin and ricin are among the most active toxins in inhibiting protein synthesis on a protein weight basis. Gelonin is 10 to 1000 times more active in inhibiting protein synthesis than the ricin A chain. Peptides like ricin and abrin are composed of two chains, an A chain which is the toxic unit and a B chain which acts by binding to cells. Unlike ricin and abrin, gelonin is composed of a single chain, and, lacking a B chain for binding to cells, is itself non-toxic to intact cells. (Stirpe, et al. *J. Biol. Chem.* 255: 6947–6953 (1980)). Mammalian cells apparently lack the ability to bind and/or to internalize the native gelonin molecule. Conjugates of gelonin to a tumor-targeting monoclonal antibody such as the monoclonal antibody 15A8 directed to an antigen present on certain tumor cells such as breast cancer cells, provides both a specific method for binding the gelonin to the cell and a route for internalization of the gelonin-antibody complex. Among the advantages of using the toxin gelonin over using toxins such as ricin A chain is its reduced toxicity to normal tissues compared to ricin A chain. Gelonin coupled to and anti-tumor associated antigen monoclonal antibody is an active and selective immunotoxic agent for tumor therapy.

Since the antibody to which the drug, toxin or radioactive label is coupled binds only to tumor cells expressing a specific antigen, only the tumor cells are killed. However, radiation from the radiolabeled compounds is not limited solely to the tumor cells in which the radiation is taken up. Radiolabelled antibodies suffer from problems which limit or complicate their use as the therapeutic agents. For example, metabolic or enzymatic degradation of the antibody may release the radiolabel and allow it to distribute to other tissues such as kidneys or bone marrow, causing unacceptable radiation damage to these organs.

SUMMARY OF THE INVENTION

The present invention provides immuno conjugates of an antibody which recognizes the 15A8 antigen on breast cancer and cervical cancer cells. In one embodiment the antibody is coupled with a toxin selected from the group consisting of gelonin, ricin A chain and abrin A chain. In another embodiment the 15A8 antibody may be coupled with a cytocidal drug such as adriamycin or a biological response modifier such as a lymphokine or cytokine. In another embodiment the antibody may be labeled with a detectable label such as a radiolabel, a chemiluminescer, a fluorescer, or an enzyme label. The cytocidal immunoconjugates are useful to treat and prevent recurrence of tumor-associated 15A8-bearing tumors by administration of these cytocidal immunoconjugates to an individual in need of such treatment. The detectably labeled 15A8 immunoconjugates are useful for diagnosis and localization of tumors by techniques known to those in the art. These labeled immunoconjugates are also useful to assay for the presence of the 15A8 antigen in biological specimens and for localizing the tumor site in vivo by means known to those of skill in the art.

One of the objects of the present invention is to provide a cytotoxic composition which would specifically bind to and kill tumor cells. Specifically, it is an object of the present invention to provide a cytotoxic composition which would specifically bind to and kill tumor cells which express the 15A8 antigen (the antigen recognized by the monoclonal antibodies disclosed and claimed in U.S. patent application Ser. No. 29,373 filed Mar. 23, 1987). Another aspect of the invention concerns a method of killing human breast cancer cells, cervical carcenoma cells, or other tumor cells expressing the 15A8 antigen by contacting the cells with a cytocidally effective amount of an immunotoxin.

It is a further object of the present invention that such a composition would be toxic to tumor cells and would cause minimal injury to normal tissue.

It is a further object of the present invention to provide a composition comprising an antibody directed to a 22 kD 15A8 tumor-associated antigen. It was a further object of the present invention to provide a labelled antibody useful in the detection, diagnosis and localization of tumors expressing the 15A8 antigen.

DESCRIPTION OF THE INVENTION

Figure 1:
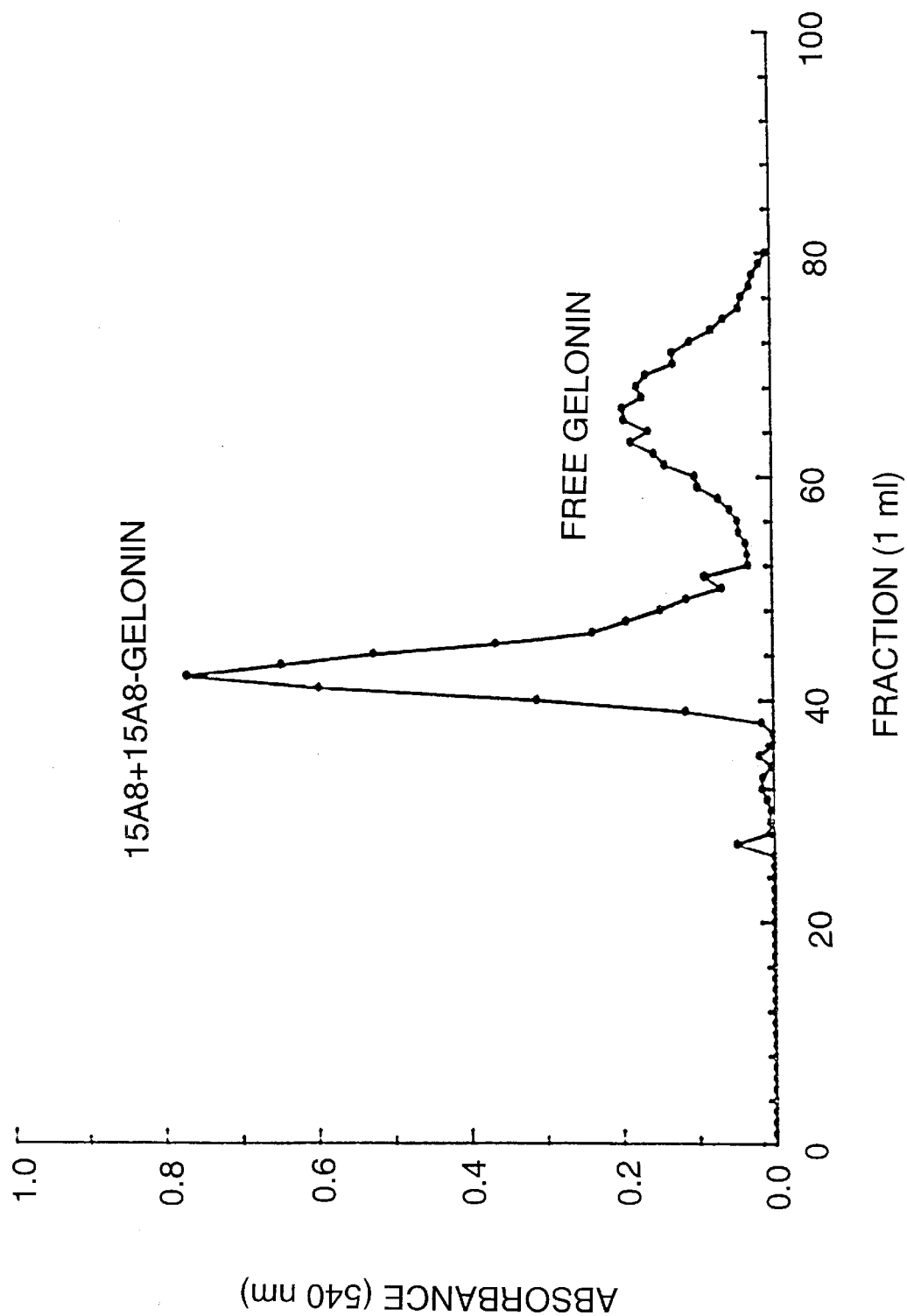
FIG. 1 is a graph which demonstrates the 15A8-gelonin elution profile by G-75 Chromatography.

As used herein the term "monoclonal antibody" means an antibody composition having a homogeneous antibody population. It is not intended to be limited as regards the source of the antibody or the manner in which it is made.

Breast carcinoma cells express a 22 kD antigen on their cell surface. Antibodies to this antigen have been produced. Specifically monoclonal antibodies of the $IgG_1$, $IgG_{2a}$ and $IgG_{2b}$ isotypes which recognize an epitope of this 22 kD antigen have been produced. Hybridomas which recognize this 22 kD (producing predominantly the $IgG_1$ isotype), 15A8 $G_{2a}$ (producing predominantly $IgG_{2a}$ isotype) and 15A8 $G_{2b}$ (producing predominantly $IgG_{2b}$ isotype). All isotype recognize the same epitope of the antigen which for the purpose of this invention will be designated the 15A8 epitope. Thus, all of these antibodies are functionally equivalent.

These representative hybridoma cultures whose cells secrete antibody of the same idiotype, i.e., all recognize the 15A8 epitope, have been deposited, at the American Type Culture Collection of 10801 University Boulevard, Manassas, Va. 20110-2209 ("ATCC") and have been assigned the accession numbers HB-8655 (for 15A8), HB-9344 (for 15A8 $G_{2a}$) and HB-9345 (for 15A8 $G_{2b}$).

These monoclonal antibodies may be made by methods known to those of skill in the art. The procedure for making the hybridoma cell cultures which produce these antibodies is described in detail in U.S. patent application Ser. No. 29,373, filed Mar. 23, 1987, which is a continuation in part of U.S. patent application Ser. No. 678,264, filed Dec. 5, 1984 and in European Application Publication 0 184 369 (published Jun. 11, 1986). Briefly, mammary tumor cells (Soule, et al, *JNCI*, 51: 1409–1413 (1973) ATCC Accession No. HTB-22) were injected into BALB/c mice intraperitoneally every three weeks for a total of three to four injections. The spleens were harvested three days after the last injection and a spleen cell suspension was prepared and washed by two centrifugations (800×g) in Dulbecco's modified Eagles medium. One hundred and eight immunized mouse spleen cells and 107 PAI myeloma cells obtained from Dr. Theo Staehlin, Basel, Switzerland, J. Stocker, *Research Disclosure*, 21713, 155–157 (1982) were resuspended for fusion in a 45% solution (v/v) of polyethylene glycol 1500. The hybrid cells were selected on hypoxanthine-aminopterin thymidine (HAT) medium.

Clones of the hybridoma were grown in vitro according to known tissue culture techniques such as is described by Cotten, et al., *Eur. J. Immunol.* 3:136 (1973). Hybridomas producing antibodies which reacted with MCF-7 and/or MDA-157 cells but not human foreskin fibroblast cells were further characterized. The antibodies produced by the 15A8 cell line and hybridomas-producing functionally equivalent antibodies reacted with the 15A8 antigen on MCF-7 cells. They also reacted with 28/31 randomly obtained human mammary carcinomas tested, and exhibited a weaker reaction with normal human epithelial cells of breast, renal proximal tubule, bladder skin, esophagus and salivary gland, but cells of substantially no other normal tissue, and was unreactive with 14 of 18 other malignant tissues tested. The 15A8 antibody also reacted with all fibrocystic diseases, normal mammary epithelium, a number of adenocarcinomas. It did not react with mesotheliomas. The 15A8 antibody crossreacts with normal breast, renal proximal tubule, epidermal, esophageal, and salivary gland epithelium and with cervical, colon and prostate carcinomas. The binding of 15A8 antibody to various tumors and tissues is summarized on Table 1 in Example 4.

As used herein with respect to the exemplified murine monoclonal anti-human breast cancer antibodies, the term "functional equivalent" means a monoclonal antibody that: (1) crossblocks an exemplified monoclonal antibody; (b) binds selectively to cells expressing the 15A8 antigen such as human breast cancer cells; (c) has a G or M isotype; (d) binds to the 15A8 antigen as determined by immunoprecipitation or sandwich immunoassay; and (e) when conjugated to gelonin, exhibits a tissue culture inhibitory dose (TCID) of at least 50% against at least one of the MCF-7, ME-180, BT-20, or A431 cell lines when used at a dose of 5–10 units per ml.

Antibody I5A8 was conjugated to gelonin using N-succinimidyl-3-(2-pyridyldithio)propionate (SPDP) or iminothiolane (IT) as a coupling agent. The conjugates were tested against Me-180, and A431 cells in a 72-hour tissue culture assay. The antibody conjugates exhibited acceptable antiproliferative activity (TCID 50% of less than 5 units/ml) against both of these cell lines.

Further details of the characterization of the antibodies are provided in the examples below.

Immunochemicals

The immunochemical derivatives of this invention that are of prime importance are immunotoxins (conjugates of the 15A8 antibody and a cytotoxic moiety or a biological response modifier) or labeled (e.g., radiolabeled, enzyme-labeled, or fluorochrome-labeled) derivatives in which the label provides a means for identifying immune complexes that include the labeled antibody.

The cytotoxic moiety of the immunotoxin may be a cytotoxic drug or an enzymatically active toxin of bacterial or plant origin (gelonin), or an enzymatically active fragment ("A chain") of such a toxin. Enzymatically active toxins and fragments threof are preferred and are exemplified by gelonin, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytoiacca americana* proteins (PAPI, PAPII, and PAP-S), momordica charantia inhibitor, curcin, crotin, saponaria officinalis innibitor, mitogellin, restrictocin, phenomycin, and enomycin. Most preferred is the conjugation with gelonin.

Biological response modifiers which may be coupled to the 15A8 antibody and used in the present invention include, but are not limited to, lymphokines and cytokines such as IL-2, interferons ($\alpha$, $\beta$, or $\gamma$), and IL-6. These biological response modifiers have a variety of effects on tumor cells. Among these effects are increased tumor cell killing by direct action as well as increased tumor cell killing by increased host defense mediated processes. Conjugation of antibody 15A8 to these biological response modifiers will allow selective localization within tumors and, hence, improved anti-proliferative effects while suppressing non-specific effects leading to toxicity of non-target cells.

Cytotoxic drugs which are useful in the present invention include, but are not limited to, adriamycin (and derivatives thereof), cis-platinum complex (and derivatives thereof), bleomycin and methotrexate (and derivatives thereof). These cytotoxic drugs are sometimes useful for clinical management of recurrent tumors and particularly breast cancer, but their use is complicated by severe side effects and damage caused to non-target cells. Antibody 15A8 may serve as a useful carrier of such drugs providing an efficient means of both delivery to the tumor and enhanced entry into the tumor cells themselves. In addition, specific antibody delivery of cytotoxic drugs to tumors will provide protection of sensitive sites such as the liver, kidney and bone marrow from the deleterious action of the chemotherapeutic agents. Use of drugs conjugated to antibody 15A8 as a delivery system allows lower dosage of the drug itself, since all drug moieties are conjugated to antibodies which concentrate within the tumor.

Conjugates of the monoclonal antibody may be made using a variety of bifunctional protein coupling agents. Examples of such reagents are SPDP, IT, bifunctional derivatives of imidoesters such as dimethyl adipimidate HCl, active esters such as disuccinimidyl suberate, aldehydes such as glutaraldehyde, bis-azido compounds such as bis(p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as a 1,5-difluoro-2,4-dinitrobenzene.

When used to kill human breast cancer cells in vitro for diagnostic purposes, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques to determine the presence or degree of breast cancer.

Cytotoxic radiopharmaceuticals for diagnosing and treating tumors carrying the 15A8 antigen such as breast cancer may be made by conjugating high linear energy transfer (LET) emitting isotopes (e.g., Y, Pr) to the antibodies. The term "cytotoxic moiety" as used herein is intended to include such isotopes.

The labels that are used in making labeled versions of the antibodies include moieties that may be detected directly, such as fluorochromes and radiolabels as well as moieties, such as enzymes, that must be reacted or derivatized to be detected. Examples of such labels are $^{32}P$, $^{125}I$, $^{3}H$, $^{14}C$, fluorescein and its derivatives, rhodamine and its derivatives, dansyl, umbelliferone, luciferia, 2,3-dihydrophthalzainediones, horseradish peroxidase, alkaline phosphatase, lysozyme, and glucose-6-phosphate dehydrogenase. The antibodies may be tagged with such labels by known methods. For instance, coupling agents such as aldehydes, carbodiimides, dimaleimide, imidates, succinimides, bis-diazotized benzadine and the like may be used to couple the antibodies with the above-described fluorescent, chemiluminescent, and enzyme labels.

The antibodies and labeled antibodies may be used in a variety of immunoimaging or immunoassay procedures to detect the presence of tumors expressing the 15A8 antigen such as breast cancer in a patient or monitor the status of such cancer in a patient already diagnosed to have it. When used to monitor the status of a cancer a quantitative immunoassay procedure may be used. Such monitoring assays are carried out periodically and the results compared to determine whether the patient's tumor burden has increased or decreased. Common assay techniques that may be used include direct and indirect assays. Direct assays involve incubating a tissue sample or cells from the patient with a labeled antibody. If the sample 15A8 antigen bearing cells such as includes breast cancer cells, the labeled antibody will bind to those cells. After washing the tissue or cells to remove unbound labeled antibody, the tissue sample is read for the presence of labeled immune complexes.

For diagnostic use the antibodies will typically be distributed in kit form. These kits will typically comprise: the antibody in labeled form in suitable containers, reagents for the incubations and washings, and substrates or derivatizing agents depending on the nature of the label. Antigen 15A8 controls and instructions may also be included.

Administration of the immunotoxins of the present invention to an individual who has been diagnosed as having a tumor with the 15A8 antigenic determinant will allow targeting and concentration of the cytotoxic agent at the site where it is needed to kill the tumor cells. By so targeting the cytotoxic agents, non-specific toxicity to other organs, tissues and cells will be eliminated or decreased.

When used in vivo for therapy, the immunotoxins are administered to the patient in therapeutically effective amounts (i.e., amounts that eliminate or reduce the patient's tumor burden). They will normally be administered parenterally, preferably intravenously. The dose and dosage regimen will depend upon the nature of the cancer (primary or metastatic) and its population, the characteristics of the particular immunotoxin, e.g., its therapeutic index, the patient, and the patient's history. The amount of immunotoxin administered will typically be in the range of about 0.1 to about 10 mg/kg of patient weight.

For parenteral administration the immunotoxins will be formulated in a unit dosage injectable form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The immunotoxin will typically be formulated in such vehicles at concentrations of about 0.1 mg/ml to 10 mg/ml.

Gelonin toxin was purified from the seeds of *gelonin multiflorinum* by the method of Stirpe, et al. supra. Briefly, gelonin was extracted from the seeds by homogenization in buffered saline solution (pH 7.4). The supernatant was concentrated after dialysis against 5 mM sodium phosphate (pH 6.5) and the gelonin further purified by ion exchange chromatography as described in Example 1. The purity of the gelonin toxin was assessed by high pressure liquid chromatography (HPLC) and sodium dodecylsulphate-polyacylamide gel electrophoreseis (SDS-Page). Gelonin toxin migrated as a single band with an approximate molecular weight of 29–30,000 daltons.

Gelonin toxin activity was measured as described in Example 2 by protein synthesis inhibition in a cell-free system.

Antibody $15A8G_2$ modified with SPDP as described in Example 5 was conjugated with iminothiolane modified gelonin as described in Examples 3 and 6. The gelonin conjugated antibody was purified as described in Example 7 by column chromatography on a Sephadex G-75 column.

The toxicity of the gelonin-conjugated antibody was determined by protein synthesis inhibition and its antiproliferative activity was determined by in vitro and in vivo tests.

The following examples provide a detailed description of the preparation, characterization, and use of the immunotoxin monoclonal antibodies of this invention. These examples are not intended to limit the invention in any manner.

EXAMPLE 1

Purification of Gelonin

Seeds of *Gelonin multiflorinum* were shelled and the nuts ground in a homogenizer with eight volumes of 0.14 M NaCl containing 5 mM sodium phosphate (pH 7.4). The homogenate was left overnight at 4° C. with continuous stirring, cooled on ice and centrifuged at 35,000 times g for 20 minutes at 0° C. The supernatant was removed, dialyzed against 5 mM sodium phosphate (pH 6.5) and concentrated using a pm10 filter. The sample was layered on a CM-52 ion-exchange column (20×1.5 cm) equilibrated with 5 mM sodium phosphate (pH 6.5). Material which bound to the ion exchange resin was eluted with 400 ml of 0 to 0.3 M linear NaCl gradient at a rate of 25 ml/hour at 4° C. Five ml fractions were collected. The fractions were monitored at 280 nm in a spectrophotometer. The gelonin eluted in about fractions 55–70 and was the last major elution peak. Fractions 55–70 were pooled, dialyzed against double distilled water and concentrated by lyophilization. The purity and the molecular weight of each preparation was checked on high pressure liquid chromatography using a TSK 3000 gel permeation column with 50 mM sodium phosphate buffer, pH 7.4 and 15% sodium dodecylsulphate-polyacrylamide gel electrophoresis (SDS-page). Gelonin migrated as a single band with an approximate molecular weight of 29–30, 000 daltons.

EXAMPLE 2

Assay of Gelonin Activity

The gelonin activity was monitored in a cell-free protein synthesis inhibition assay. The cell-free protein synthesis inhibition assay was performed by sequentially adding to 50 $\mu$l rabbit reticulocyte lysate, thawed immediately before use, mixing after each addition, the following components: 0.5 ml of 0.2 M Tris HCl (pH 7.8), 8.9 ml of ethylene glycol, and 0.25 ml of 1 M HCl).

Twenty microliters of a salt-amino acid-energy mixture (SAEM) consisting of: 0.375 M KCl, 10 mM Mg $(CH_3CO_2)_2$, 15 mM glucose, 0.25–10 mM amino acids (excluding leucine), 5 mM ATP, 1 mM GTP, 50 mM Tris-HCl (pH 7.6), 10 ul Creatinine phosphate-creatinine phosphokinase, 8 ul $^{14}C$ leucine (Amersham, 348 mCi/mmol), and adding 1.5 ul of solutions containing varying concentrations of the Gelonin mixture. The mixture was incubated for 60 minutes at 30° C. $^{14}C$-leucine incorporation was monitored in an aliquot of the mixture by precipitating synthesized protein on glass fiber filters, washing in 10% TCA and acetone, and monitoring the radioactivity in a Beta-counter using Aquasol scintillation fluid. Gelonin with a specific activity no lower than $4 \times 10^9$ U/mg was used for conjugation with the antibodies. A unit of gelonin activity is the amount of gelonin protein which causes 50% inhibition of incorporation of $[^{14}C]$ leucine into protein in the cell free assay.

EXAMPLE 3

Modification of Gelonin with Iminothiolane

Gelonin in phosphate buffered saline was concentrated to approximately 2 milligrams/ml in a Centricon 10 microconcentrator. Triethanolamine hydrochloride (TEA/HCl), pH 8.0 and EDTA were added to a final concentration of 60 mM TEA/HCl and 1 mM EDTA pH 8.0. 2-Iminothiolane stock solution (20 mM) was added to a final concentration of 1 mM and the sample was incubated for 90 minutes at 4° C. under a stream of nitrogen gas.

Excess iminothiolane was removed by gel filtration on a column of Sephadex G-25 (1×24 cm) pre-equilibrated with 5 mM bis-tris/acetate buffer, pH 5.8 containing 50 mM NaCl and 1 mM EDTA. Fractions were analyzed for protein content in microtiter plates using the Bradford dye binding assay. Briefly, forty microliters of sample, 100 ul of phosphate buffered saline (PBS) and 40 ul of dye concentrate were added to each well. Absorbance at 600 mm was read on a Dynatech Microelisa Autoreader. Gelonin elutes at the void volume (about fractions 14–20). These fractions are pooled and concentrated by use of a Centricon-10 microconcentrator.

EXAMPLE 4

Preparation and Characterization of Monoclonal Antibody to 15A8 Breast Cancer Antigen Monoclonal antibodies may be made by methods known to those of skill in the art. The procedure for making the hybridoma cell cultures which produce these antibodies is described in detail in U.S. patent application Ser. No. 29,373, filed Mar. 23, 1987, which is a continuation in part of U.S. patent application Ser. No. 678,264, filed Dec. 5, 1984 and in European Application Publication 0 184 369 (published Jun. 11, 1986). Briefly, mammary tumor cells (Soule, et al, *JNCI*, 51: 1409–1413 (1973) ATCC Accession No. HTB-22) were injected into BALB/c mice intraperitoneally every three weeks for a total of three to four injections. The spleens were harvested three days after the last injection and a spleen cell suspension was prepared and washed by two centrifugations (800×g) in Dulbecco's modified Eagles medium. One hundred and eight immunized mouse spleen cells and 107 PAI mezeloma cells obtained from Dr. Theo Staehlin, Basel, Switzerland, J. Stocker, *Research Disclosure*, 21713, 155–157 (1982) were resuspended for fusion in a 45% solution (v/v) of polyethylene glycol 1500. The hybrid cells were selected on hypoxanthine-amenopterin thymidine (HAT) medium.

Clones of the hybridoma were grown in vitro according to known tissue culture techniques such as is described by Cotten, et al., *Eur. J. Immunol.* 3:136 (1973). Hybridomas producing antibodies which reacted with MCF-7 and/or MDA-157 cells but not human foreskin fibroblast cells were further characterized. The antibodies produced by the 15A8 cell line and hybridomas-producing functionally equivalent antibodies reacted with the 15A8 antigen on MCF-7 cells. They also reacted with 28/31 randomly obtained human mammary carcinomas tested, and exhibited a weaker reaction with normal human epithelial cells of breast, renal proximal tubule, bladder skin, esophagus and salivary gland, but cells of substantially no other normal tissue, and was unreactive with 14 of 18 other malignant tissues tested. The 15A8 antibody also reacted with all fibrocystic diseases, normal mammary epithelium, a number of adenocarcinomas. It did not react with mesotheliomas. The 15A8 antibody crossreacts with normal breast, renal proximal tubule, epidermal, esophageal, and salivarcy gland epithelium and with cerviaal, colon and protratee carcinomas. The binding of 15A8 antibody to various tumors and tissues is summarized in Table 1 below:

TABLE 1

Binding of 15A8 Antibody to Tissues and Tumors

|  | 15A8 |
| --- | --- |
| CELL LINES (live) | |
| Mammary carcinoma | |
| MCF-7 | + |
| MDA-157 | + |
| DU4475 | − |
| Non-Mammary | |
| HFF | − |
| PAI | − |
| TISSUES (frozen) | |
| Human mammary carcinoma (total) | + (28/31) |
| Primary infiltrating ductal carcinoma | + (16/19) |
| Infiltrating ductal cancer metastatic to liver, lung omentum and brain | + (5/5) |
| Intraductal papillary, colloid mammary carcinomas | + (6/6) |
| Comedo carcinoma | + (1/1) |
| Cystosarcoma phylloides | − (1) |

TABLE 1-continued

Binding of 15A8 Antibody to Tissues and Tumors

|  | 15A8 |  |
| --- | --- | --- |
| Papillary ductular hyperplasia sclerosins adenosis | + | (2/2) |
| Fibrocystic disease | + | (2/2) |
| Fibroadenoma | + | (2/2) |
| Normal mammary epithelium | + | (4/4) |
| NORMAL TISSUES | | |
| Epidermis | + | |
| Salivary gland | + | |
| Thyroid | − | |
| Adrenal | − | |
| Lung | − | |
| Bronchus | − | |
| Heart | − | |
| Aorta | − | |
| Esophagus | + | |
| Stomach | − | |
| Small bowel | − | |
| Large bowel | − | |
| Liver (2) | − | |
| Pancreas | − | |
| Gall bladder | − | |
| Spleen | − | |
| Lymph nodes | − | |
| Kidney (2) | prox tubule + | |
| Bladder | − | |
| Ovary | − | |
| Testis | − | |
| Cervix | − | |
| Uterus | − | |
| Bone marrow | − | |
| Brain | − | |
| NON-MAMMARY MALIGNANCIES | | |
| Lung | | |
| Squamous cell cancer | + | |
| Adenocarcinoma | − | |
| Small cell cancer | − | |
| Gastrointestinal | | |
| Gastric cancer | − | |
| Cholangiocarcinoma | − | |
| Pancreatic cancer | − | |
| Colon cancer | −/+ | |
| Genito-urinary | | |
| Cervix cancer | + | |
| Ovarian cancer | − | |
| Bladder cancer | − | |
| Renal cancer | − | |
| Prostate cancer (2) | −/+ | |
| Lymphoma | | |
| T cell | − | |
| Mesothelioma | − | |
| Melanoma | − | |

+ = positive immuoperoxidase reaction (usually strong)
− = no reaction
± = weak reaction

EXAMPLE 5

Modification of Monoclonal Antibody 15A8 with SPDP

N-succinimidyl 3-(2-pyridyldithio) (propionate) in dimethylformamide was prepared as a stock solution of 3 mg/ml in dry dimethylforamide. Since the crystalline SPDP can undergo hydrolysis, the actual concentration of chemically reactive crosslinker was determined by spectrophotometric methods by analyzing the absorbance at 260 nm in a dual-beam spectrophotometer. The concentration of SPDP stock is calculated from the following equation:

$$\frac{\text{Change in absorbance (260 nm)}}{0.02 \times 10^3 \text{ ml/mmol}} \times \frac{(3.01)}{0.01} = \text{mmoles/ml/SPDP}$$

One milligram of monoclonal antibody 15A8 in 0.5 ml of PBS was added to a glass tube. SPDP stock solution was slowly added at a 5-fold molar excess to the tube, mixing constantly. The mixture was incubated for 30 minutes at room temperature, mixing every 5 minutes during the incubation period.

Excess unreacted SPDP was removed by gel filtration chromatography on a Sephdex G-25 column (1×24 cm) pre-equilibrated with PBS. Fractions (0.5 ml) were collected during the PBS elution and were analyzed for protein content by the Bradford dye method. Antibody eluted in the void volume (approximately fractions 14–20). These fractions were pooled and the protein concentrated in a Centricon-30 microcentrator. The Centricon retentate was washed with 100 mM sodium phosphate buffer, pH 7.0 containing EDTA (0.5 mM). The antibody was concentrated to a final volume of approximately 0.5–0.75 ml.

EXAMPLE 6
Conjugation of SPDP-Modified Monoclonal Antibody 15A8 With Iminothiolane-modified Gelonin Monoclonal antibody 15A8 modified as described in Example 4 was mixed with an equal weight of gelonin modified as in Example 3. This proportion corresponded to a 5-fold molar excess of gelonin as compared to antibody. The pH of the mixture was adjusted to 7.0 by the addition of 0.05 M TEA/HCl buffer pH 8.0 and the mixture was incubated for 20 hours at 4° C. under nitrogen. Iodoacetamide (0.1 M) was added to a final concentration of 2 mM to block any remaining free sulfhydryl groups and incubation was continued for an additional hour at about 25° C. The reaction mixture was stored at 4° C. until purification by gel filtration.

EXAMPLE 7
Purification of Gelonin-Monoclonal Antibody 15A8 Complexes

Non-conjugated gelonin was removed from the reaction mixtures of Example 6 by gel filtration on a Sephadex G-75 column (1.6×31 cm) pre-equilibrated with PBS.

Reaction mixtures from Example 6 were concentrated to approximately 1 ml with a Centricon 30 microconcentrator before loading on the Sephadex column. The column was washed with PBS. One ml fractions were collected and 50 ul aliquots are analyzed for protein by the Bradford dye binding assay. M. Bradford, *Anal. Biochem* 72:248 (1976).

Free- and gelonin-conjugated antibody eluted in the void volume (about fractions 17–23) while, unconjugated gelonin elutes at about fractions 35–41. FIG. 1 demonstrates the elution profile of the G-75 column. FIG. 1 demonstrates the elution profile and demonstrates that gelonin can be separated from gelonin-antibody conjugate and unconjugated antibody, both of which coelute in the first peak (about fractions 38–52). This elution pattern was confirmed by electrophoresis of 50 ul aliquots on 5–20% gradient non-reducing SDS polyacrylamide gels as shown on FIG. 2. The coupling mixture was loaded on lane 3. Bands for free gelonin, free antibody and for one molecule of gelonin coupled per molecule of antibody and two molecules of gelonin coupled per antibody molecule are shown. The void volume peak of the G-75 column containing free antibody and antibody-gelonin conjugate was loaded on lane 4.

Figure 2:
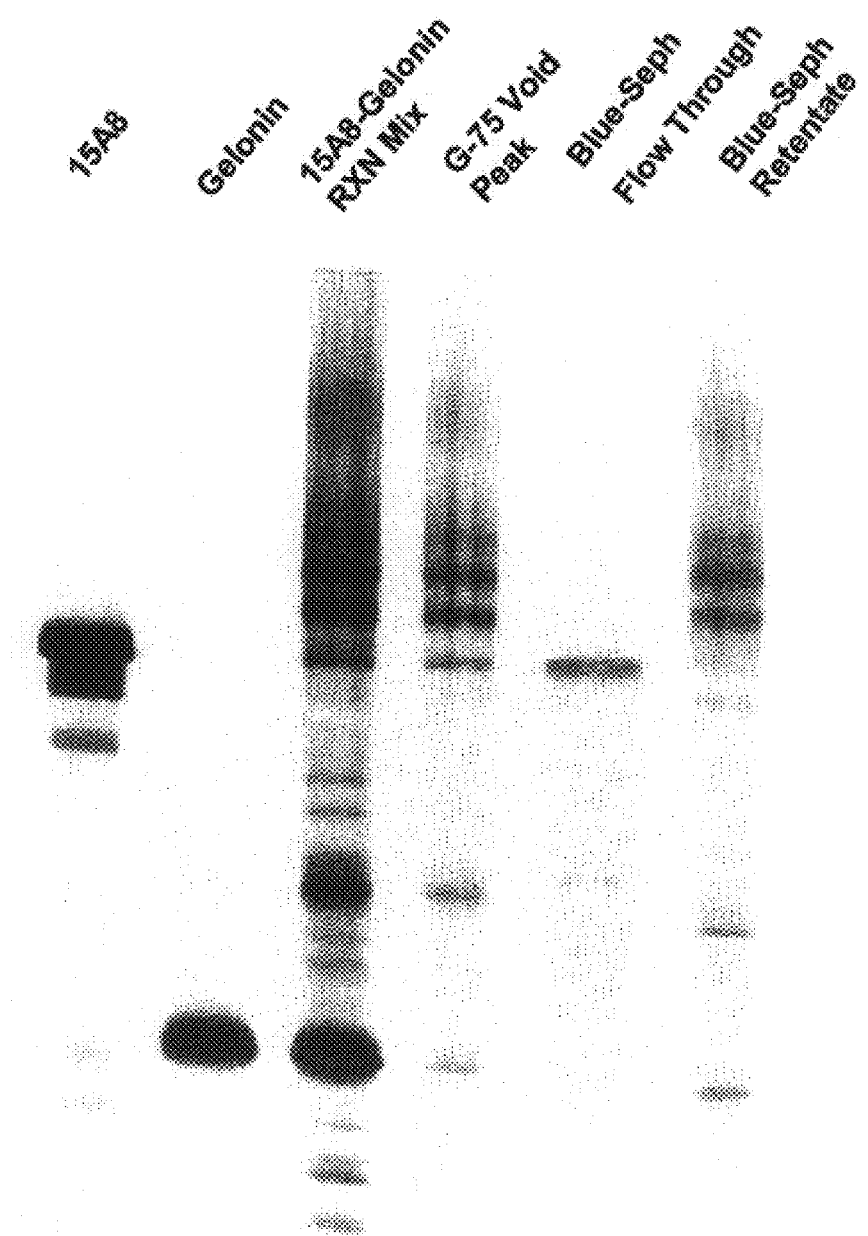
FIG. 2 demonstrates the electrophoretic pattern of the 15A8-gelonin complex.
Figure 3:
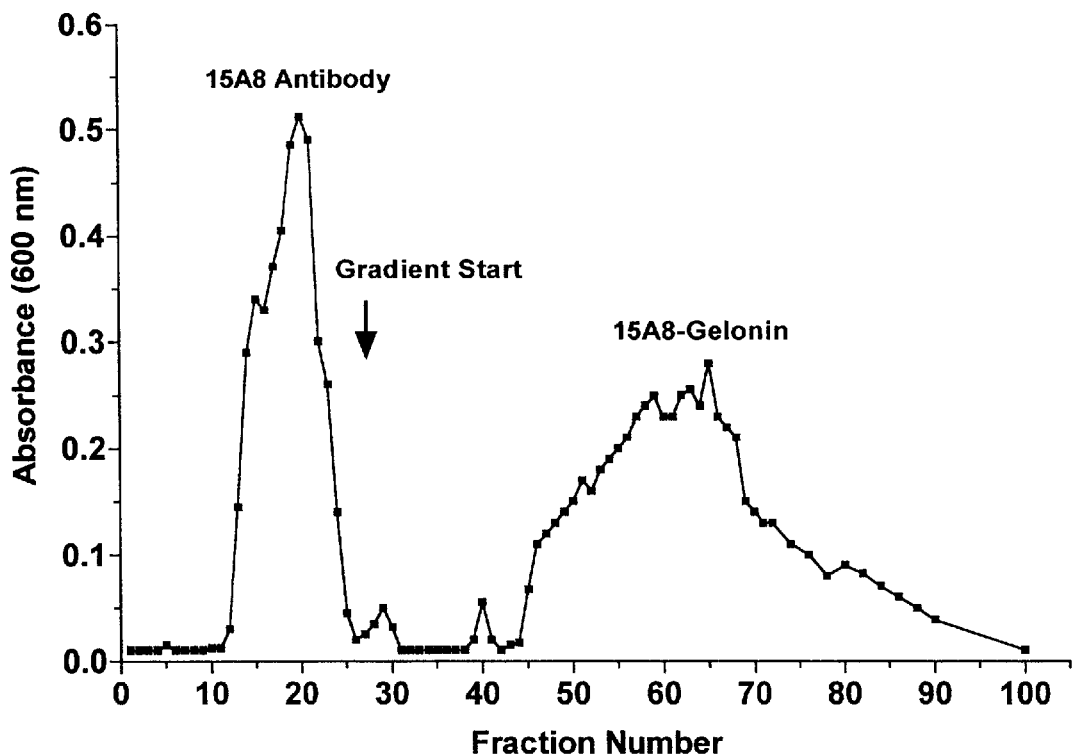
FIG. 3 is a graph of the chromatographic elution profile of the G-75 eluate on Blue Sepharose.

Non-conjugated antibody was removed from the gelonin conjugated antibody by affinity chromatography on a column (1×24 cm) of Blue Sepharose CL-6B pre-equilibrated with 10 mM phosphate buffer, pH 7.2 containing 0.1 M NaCl. After loading the G-75 eluate sample, the column was washed with 30 ml of the same buffer to completely elute non-conjugated antibody. Gelonin-conjugated antibody bound to the column and was eluted with a linear salt gradient of 0.1 to 2 M NaCl in 10 mM phosphate buffer, pH 7.2. The antibody-gelonin complex eluted at approximately 0.7 M NaCl as shown on FIG. 3 which depicts the elution profile of the Blue Sepharose column. The flow-through peak contains only free antibody (FIG. 2, lane 5) while fractions 50–80, eluted with high salt, contain 15A8-gelonin conjugate free of unconjugated gelonin or antibody (FIG. 2, lane 6).

Protein content of the eluted fractions was determined by the Bradford dye binding assay. The protein-containing fractions were pooled and the elution pattern confirmed by electrophoresis on a 5 to 20% gradient non-reducing polyacrylamide gel. The electrophoretic pattern of the 15A8-gelonin complex is shown on FIG. 2.

Figure 4:
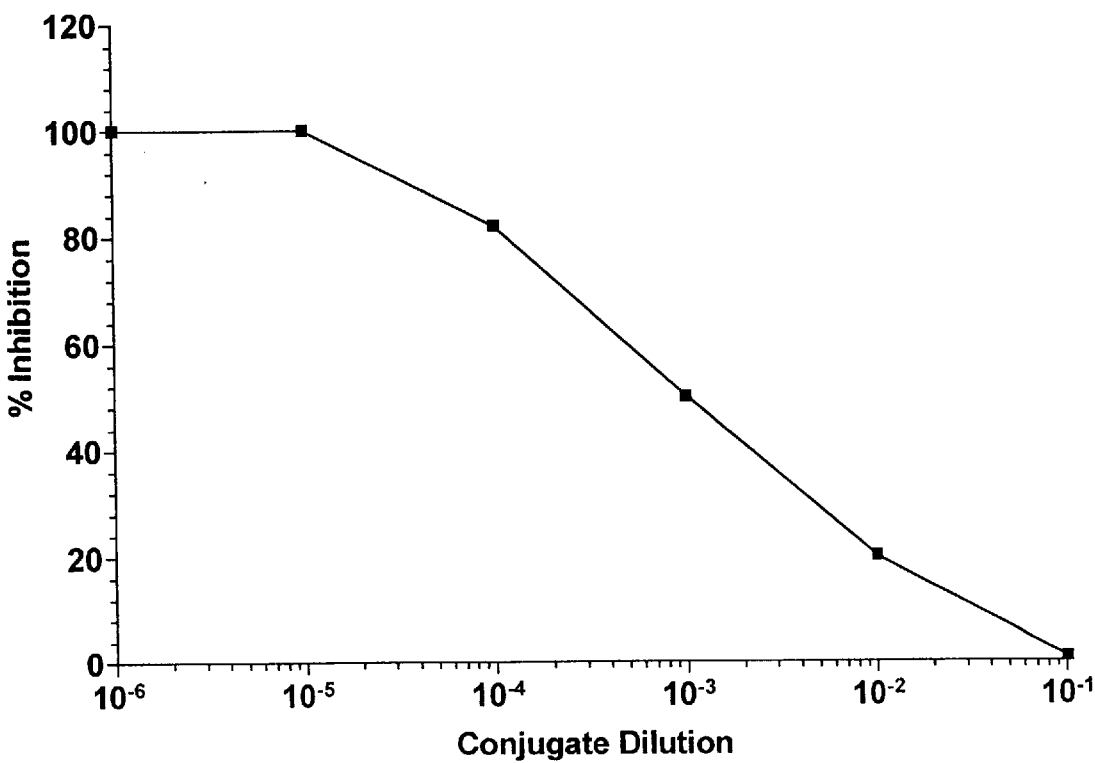
FIG. 4 demonstrates the protein synthesis inhibitory activity of the gelonin-15A8 antibody complex.

The rabbit reticulocyte in vitro translation system described in Example 3 was utilized to estimate the gelonin activity of the essentially pure gelonin-15A8 antibody complex. As shown on FIG. 4 the essentially pure gelonin-15A8 antibody is active in the reticulocyte lysate assay. A 1:1000 dilution of the original sample caused approximately a 50% inhibition of protein synthesis, i.e., a 50% reduction of the incorporation of $^{14}$C-leucine into protein. Thus, the activity of the original preparation was 1000 U/ml.

EXAMPLE 8
Comparison of Binding of Gelonin-conjugated and Unconjugated 15A8 Antibody to Target Cells The ability of the gelonin-conjugated and unconjugated 15A8 antibody to bind to target cells was assessed. Fifty thousand target cells (Me-180) or non-target human melanoma cells (AAB-527 cells) were added to each well of microtiter plate. The cells were dried on the plates overnight at 37° C. The cells were then washed with three changes of cold PBS and air dried overnight. The cell surface antigenic determinants remain antigenically active after this treatment.

After attachment of the cells, the plates were washed with Washing Buffer (9.68 Tris, 64.8 sodium chloride, 16 ml Tween 20, 800 mg thimerasol in 8 l of double distilled water). Antibody samples were diluted in Washing Buffer containing 1% Bovine serum albumin (w/v) (Diluting buffer). Fifty microliters of various concentrations ranging from 0.05 to 50 ug/ml of either conjugated or unconjugated 15A8 antibody were added to the wells. After incubation for 1 hour at 4° C., the supernantants are removed and the wells washed twice with Washing Buffer.

Fifty microliters per well of horseradish peroxidase conjugated goat anti-mouse IgG obtained from Bio-rad and diluted 1:1000 (v/v) (HPGAM) in Diluting Buffer was added to each well. The plates were incubated for 1 hour at 4° C. and the wells washed twice with Washing Buffer. After incubation of the plates with 50 ul of Substrate Solution (80 mM citrate phosphate (pH 5.0), 1 mM o-phenylenediane (ABTS) and 4 ul of 30% hydrogen peroxide) in the dark for 30 minutes at room temperature, 25 ul of 4 N sulfuric acid was added to each well. The absorbance at 492 nm was determined on an Elisa scanner.

Figure 5:
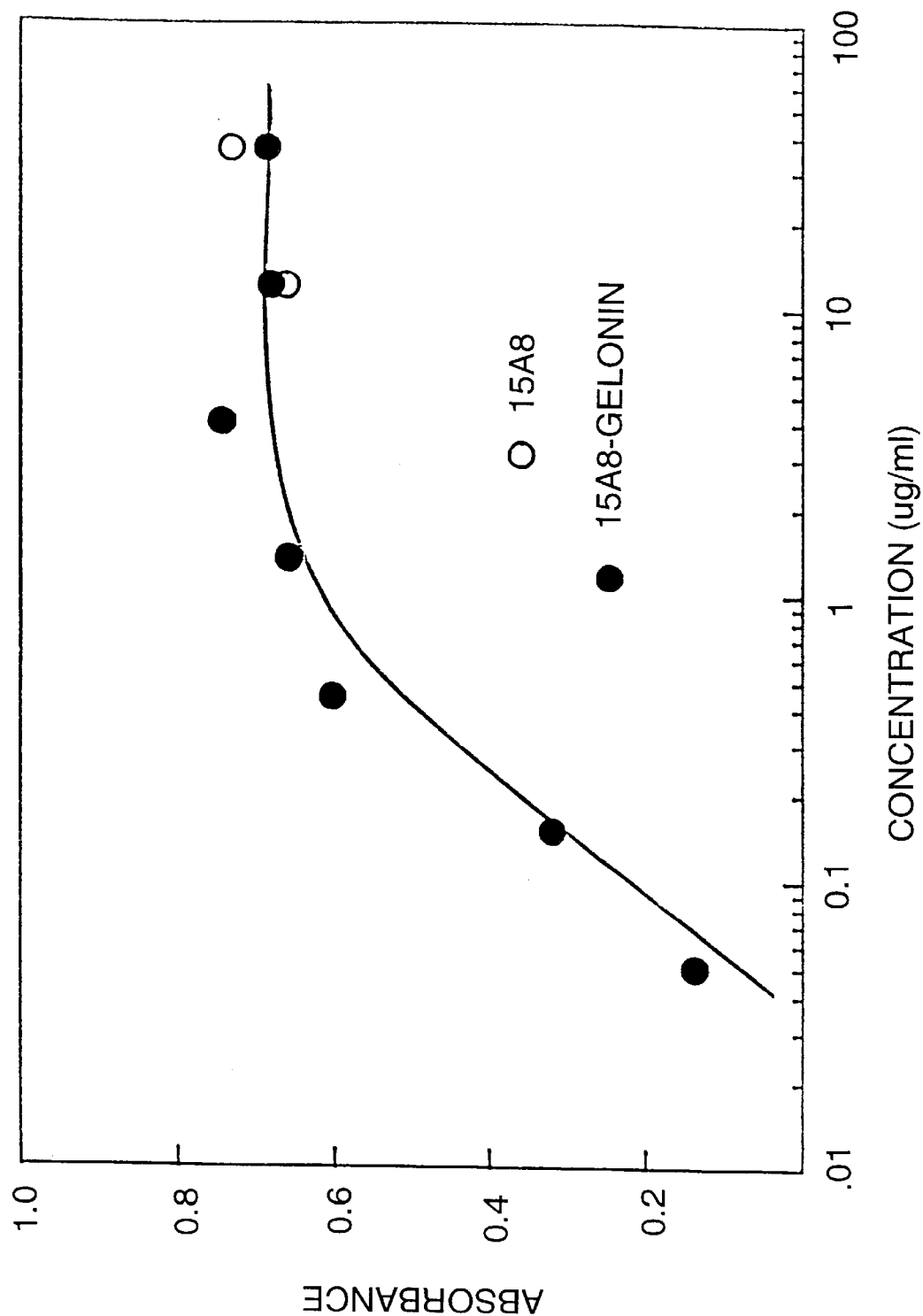
FIG. 5 demonstrates the binding of the free 15A8 antibody complex to Me-180 cells.

The results are shown on FIG. 5. The 15A8 gelonin complex bound to Me-180 target cells to the same extent as did native 15A8 antibody. Since there was no difference in the binding of the 15A8-gelonin or the unconjugated 15A8 antibody to the Me-180 antigen containing target cells, the chemical conjugation procedure does not alter the affinity of the antibody for its target antigen. There was no detectable binding of either 15A8 or 15A8 gelonin complex to non-target AAB527 melanoma cells.

EXAMPLE 9

Antiproliferative Effects of Gelonin and Gelonin-15A8 Antibody Complex

Figure 6:
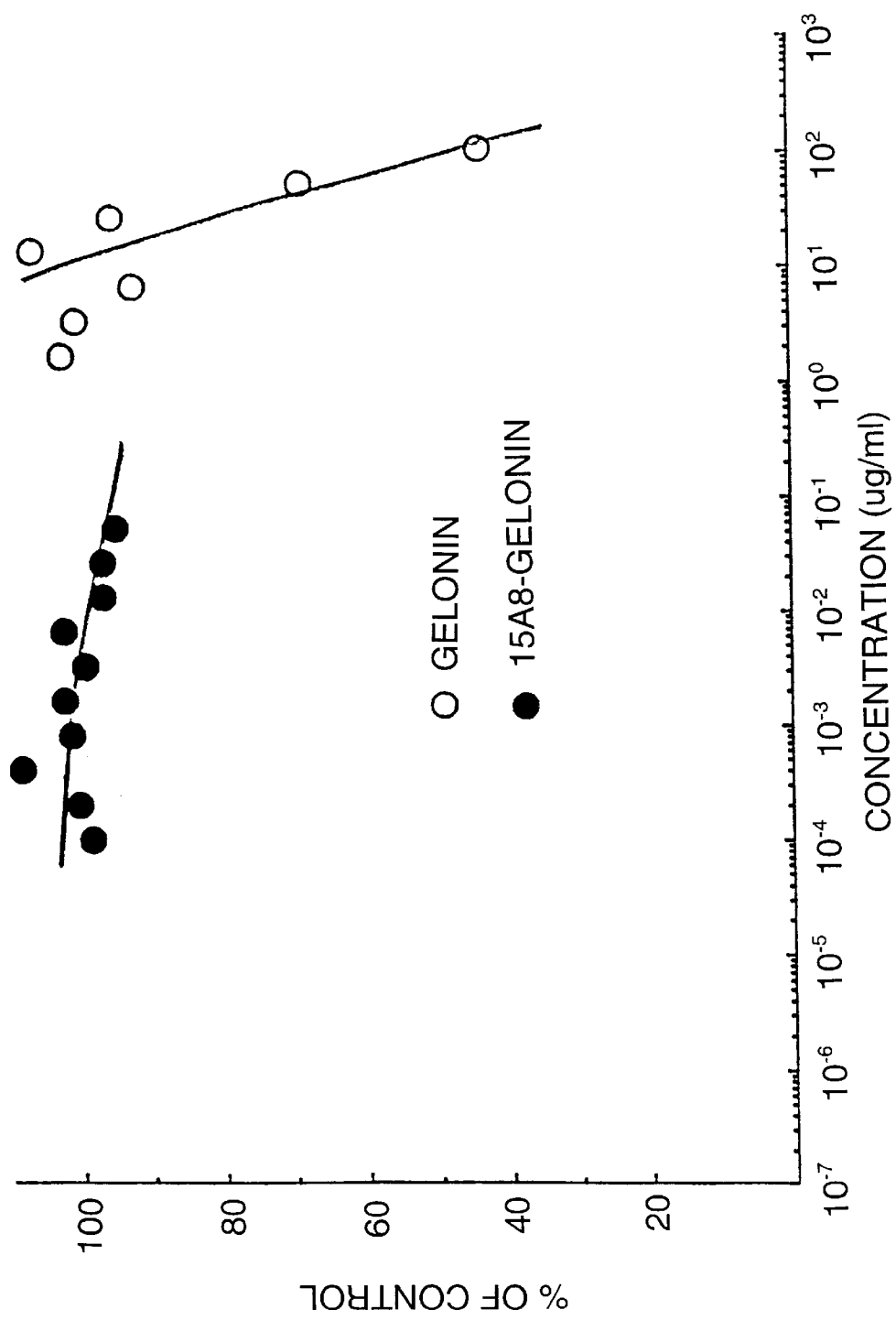
FIG. 6 demonstrates the anti-proliferative activity of 15A8-gelonin complex on non-target HS 294% cells.

The antiproliferative effects of gelonin and 15A8-gelonin complex was assessed by plating approximately 5,000 cells/well in microtiter plate in 200 µl of appropriate tissue culture media. The cells were allowed to adhere for 24 hours at 37° C. in atmosphere of 5% $CO_2$ in air. Non-targeted, antigen negative HS294 melanoma cells, antigen positive Me-180 and A-431 squamous carcinoma cells in log-phase were treated with various concentrations of either media alone (control), gelonin or 15A8-gelonin conjugate and incubated at 37° C. in an atmosphere of 5% $CO_2$ in air for 72 hours. The plates were washed three times with cold PBS. 50 µl of methanol was added to each well and the cells lysed by repeated cycles of freezing and thawing. Protein concentrations were then determined by the Bradford dye test. Cell growth inhibition was assessed by reduction in protein concentrations of treated cells as compared to saline-treated controls. As shown in FIG. 6, there was no inhibition of cell growth by the 15A8-gelonin conjugate on non-targeted HS294t melanoma cells. Me-180 target cells were 7 logs and 5 logs respectively more sensitive to the 15A8-gelonin immunotoxin than to gelonin alone (FIGS. 7 and 8, respectively).

Figure 7:
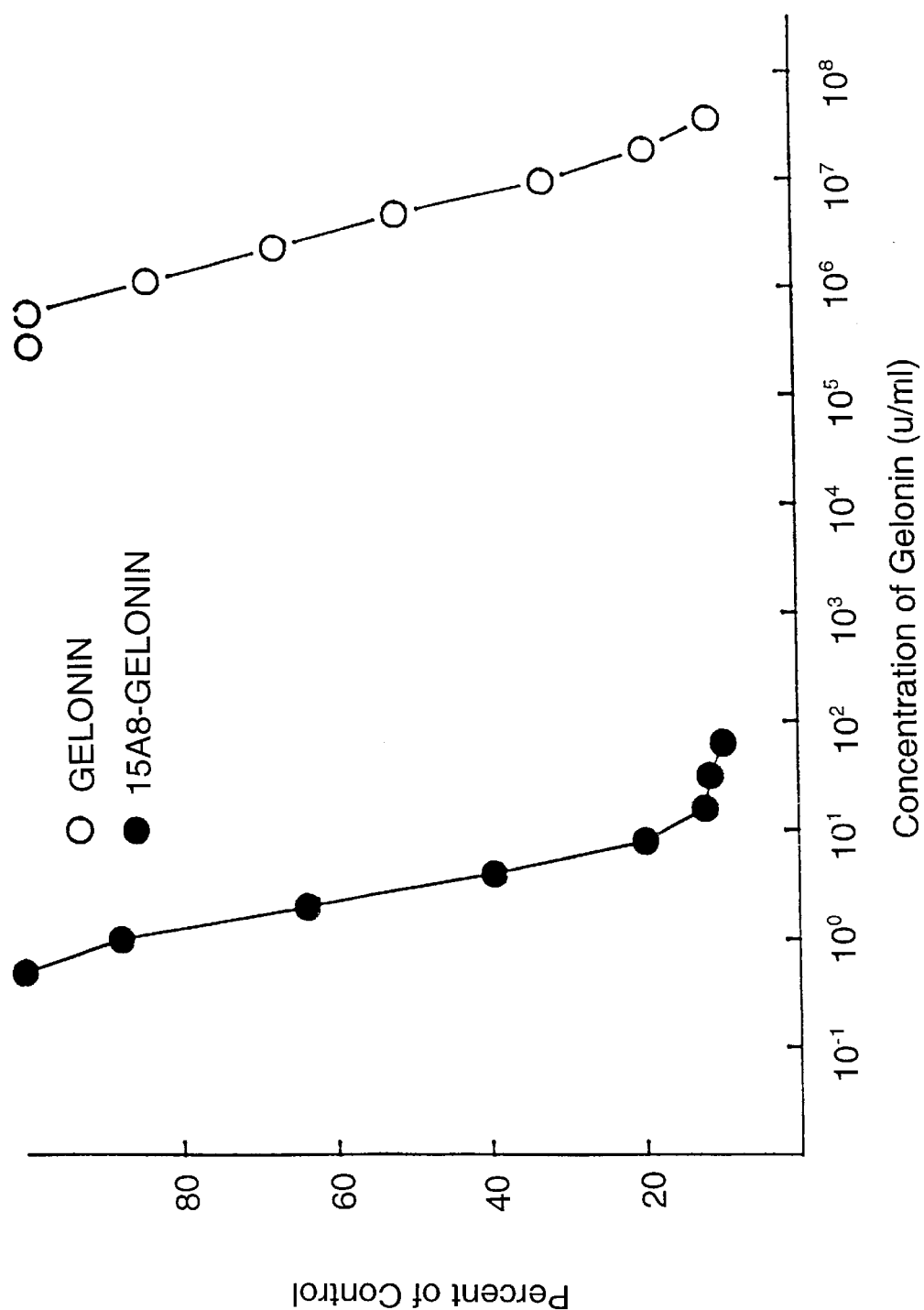
FIG. 7 demonstrates the antiproliferative activity of gelonin and gelonin-15A8 antibody complex on Me-180 cells.
Figure 8:
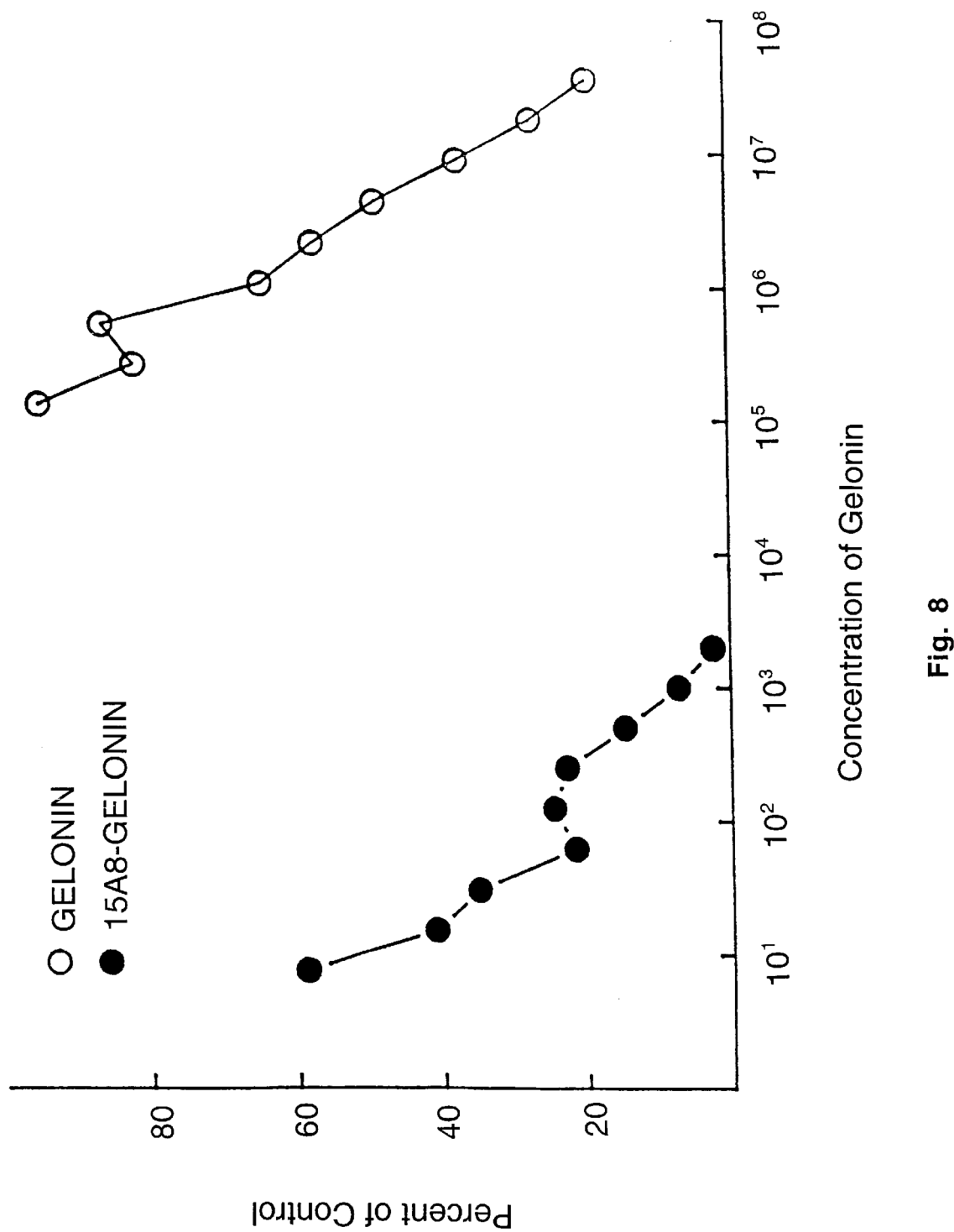
FIG. 8 demonstrates the antiproliferative activity of gelonin and gelonin-15A8 antibody complex on A431 cells.

FIG. 7 demonstrates that at approximately 5 U/ml, gelonin conjugated 15A8 antibody inhibited 50% of the Me-180 cells, while a concentration of $10^7$ U/ml of the unconjugated gelonin was required to achieve the same effect.

Similar results were obtained with A431 cells, an epidermoid carcinoma 15A8 antigen positive cell line. As shown on FIG. 8 the gelonin 15A8 antibody complex killed cells at approximately 5 log lower concentration than did the free toxin.

Since only cells containing the 15A8 antigen on their surface were killed by the gelonin 15A8 immunotoxin, this immunotoxin is an efficient method to target and kill 15A8 tumor associated antigen containing cells while minimizing or preventing damage or injury to normal non-tumor associated antigen-bearing cells.

EXAMPLE 10

Effect of Gelonin 15A8 Antibody Conjugate In Vivo

Antibody 15A8 conjugated with gelonin or gelonin alone (as a control) were tested for their antitumor activity against a highly tumorigenic variant of the human breast cancer cell lines MW (Chu, et al., *Cancer Research* 45:1357–1366). Female athymic BALB/c nu/nu mice (20–24 g) were injected in the right axillary region with $1.25 \times 10^7$ cells per animal in 0.5 ml. Three days later, 200 ul of 15A8-gelonin complex or free gelonin in Dulbecco's Modified Eagle Medium containing 50 ng/ml hydrocortisone and insulin at concentrations of $10^{-7}$ M, $3 \times 10^{-7}$ M, $6 \times 10^{-7}$ and $10^{-6}$ M were injected by the tail vein to give appoxmate plasma concentrations of $10^{-8}$ M, $3 \times 10^{-8}$ M, $6 \times 10^{-8}$ M and $10^{-7}$ M. Four weeks later tumor sizes were measured using calipers and at five weeks post-injection tumors were removed and weighed. The results are shown on Table 2.

TABLE 2

Comparison of In Vivo Effects Produced by Gelonin-15A8 Antibody Conjugate and Free Gelonin

| In Vivo Conc. (M) | Volume (cm) | Weight (gm) |
|---|---|---|
| Free Gelonin | | |
| $10^{-8}$ | 2.50 | 2.55 |
| $10^{-8}$ | 4.00 | 3.87 |
| $3 \times 10^{-8}$ | 0.86 | 0.54 |
| $3 \times 10^{-8}$ | 1.66 | 1.66 |
| $6 \times 10^{-8}$ | 1.46 | 1.48 |
| $6 \times 10^{-8}$ | 5.42 | 5.05 |
| $10^{-7}$ | 4.75 | 3.51 |
| $10^{-7}$ | 2.39 | 1.53 |
| | 23.11 | 20.19 |
| Conjugate | | |
| $10^{-8}$ | 0.15 | 0.21 |
| $10^{-8}$ | 3.02 | 1.86 |
| $3 \times 10^{-8}$ | 0.14 | 0.14 |
| $3 \times 10^{-8}$ | 1.87 | 2.18 |
| $6 \times 10^{-8}$ | 1.88 | 2.54 |
| $6 \times 10^{-8}$ | 3.15 | 1.50 |
| $10^{-7}$ | 1.69 | 1.69 |
| $10^{-7}$ | 5.24 | 4.27 |
| | 17.24 | 14.39 |

The concentration of the gelonin or gelonin 15A8 conjugate was approximated assuming a ten-fold dilution of the injected dose in the blood volume of the animal. Based on the average tumor size and average tumor weight, the conjugate 15A8-gelonin reduced tumor growth to approximately 70%–75% of the tumor size and weight with the control unconjugated gelonin as shown below:

Tumor Size at four weeks:

$$\frac{15A8\text{-gelonin conjugate}}{\text{Gelonin}} = \frac{17.24}{23.11} = 75\%$$

Tumor Weight at five weeks:

$$\frac{15A8\text{-gelonin conjugate}}{\text{Gelonin}} = \frac{14.39}{20.19} = 71\%$$

Thus, it can be seen that with only one administration of the gelonin-15A8 complex the tumor size was reduced to 70%–75% of the tumor size with the control unconjugated gelonin. More frequent injections of the immunotoxin should be even more effective at reducing tumor burden.

One skilled in the art will readily appreciate that the present invention is well adapted to carry out the objects and obtain the ends and advantages mentioned, as well as those inherent therein. The compounds, methods, procedures and techniques described herein are presently representative of the preferred embodiments, are intended to be exemplary, and are not intended as limitations on the scope of the present invention. Changes therein and other uses will occur to those skilled in the art which are encompassed within the spirit of the invention and are defined by the scope of the appended claims.

What is claimed is:

1. A composition of matter comprising a 15A8 antibody conjugated to an amino group of a gelonin moiety.

2. A method of delivering toxin to breast cancer cells that express the 15A8 tumor associated antigens, said method comprising the step of administering to an individual an anti-15A8 monoclonal antibody coupled to a gelonin.

3. A method of delivering toxin to cervical cancer cells that express the 15A8 tumor associated antigens, said method comprising the step of administering to an individual an anti-15A8 monoclonal antibody coupled to a gelonin.

4. A ex vivo or in vitro method of killing human cervical cancer cells expressing the 15A8 antigen, said method comprising the step of administering an anti-15A8 antibody conjugated to an amino group of gelonin.

* * * * *

UNITED STATES PATENT AND TRADEMARK OFFICE
CERTIFICATE OF CORRECTION

PATENT NO. : 6,669,938 B1 Page 1 of 1
DATED : December 30, 2003
INVENTOR(S) : Michael G. Rosenblum It is certified that error appears in the above-identified patent and that said Letters Patent is hereby corrected as shown below:

Title page,
Item [54], Title, "IMMUNOCONJUCATES" should read
-- IMMUNOCONJUGATES. --.

Column 4,
Line 5, "isotype" should read -- isotypes --.

Column 5,
Line 5, please insert a space before "propionate".
Line 12, please insert a blank line before "Immunochemicals"
Line 25, "threof" should read -- thereof --.

Column 9,
Line 33, "was" should read -- were --.
Line 39, "salivarcy" should read -- salivary --.
Line 40, "cerviaal" should read -- cervical --
Line 40, "protratee" should read -- prostate --.

Column 13,
Line 10, "was" should read -- were --.
Line 63, "appoximate" should read -- approximate --.

Signed and Sealed this

Twenty-ninth Day of June, 2004

JON W. DUDAS
*Acting Director of the United States Patent and Trademark Office*